United States Patent
Kracker et al.

(10) Patent No.: US 12,226,644 B2
(45) Date of Patent: Feb. 18, 2025

(54) INHIBITION OF ONSET OF CARDIAC TACHYARRHYTHMIA WITH INTERCOSTAL NERVE STIMULATION

(71) Applicant: Medtronic, Inc., Minneapolis, MN (US)

(72) Inventors: Stefan G. Kracker, Sonthofen (DE); Lilian Kornet, Eijsden (NL); Michelle M. Galarneau, Eagan, MN (US); Matthew D. Bonner, Plymouth, MN (US); Johan Maas, Winterswijk (NL); Berthold Stegemann, Kassel (DE); Paulus C. van Venrooij, Hoensbroek (NL); Vasiliki Spyropoulou, Bologna (IT); Victor Peter Jozef Duijsens, Grevenbicht (NL); Markus J. C. Lazeroms, Vroenhoven-Reimst (NL)

(73) Assignee: Medtronic, Inc., Minneapolis, MN (US)

( * ) Notice: Subject to any disclaimer, the term of this patent is extended or adjusted under 35 U.S.C. 154(b) by 277 days.

(21) Appl. No.: 17/661,649

(22) Filed: May 2, 2022

(65) Prior Publication Data
US 2022/0362568 A1    Nov. 17, 2022

Related U.S. Application Data

(60) Provisional application No. 63/188,278, filed on May 13, 2021.

(51) Int. Cl.
*A61N 1/39* (2006.01)
*A61B 5/363* (2021.01)

(52) U.S. Cl.
CPC ............ *A61N 1/3987* (2013.01); *A61B 5/363* (2021.01); *A61N 1/39622* (2017.08)

(58) Field of Classification Search
CPC .............. A61N 1/3987; A61N 1/39622; A61N 1/0504; A61N 1/36139; A61N 1/36175;
(Continued)

(56) References Cited

U.S. PATENT DOCUMENTS 7,684,864 B2    3/2010  Olson et al.
8,301,233 B2   10/2012  Zhang et al.
(Continued)

OTHER PUBLICATIONS

Buiten et al., "Subcutaneous Electrical Nerve Stimulation: A Feasible and New Method for the Treatment of Patients With Refractory Angina," Neuromodulation: Technology at the Neural Interface, vol. 14, No. 3, May-Jun. 2011, pp. 258-265.
(Continued)

*Primary Examiner* — Yingchuan Zhang
*Assistant Examiner* — Sebastian X Lukjan
(74) *Attorney, Agent, or Firm* — Shumaker & Sieffert, P.A.

(57) ABSTRACT

An example medical device includes a plurality of electrodes, therapy delivery circuitry, and processing circuitry configured to control the therapy delivery circuitry to deliver electrical stimulation to an intercostal nerve of a patient via at least two of the plurality of electrodes, wherein the electrical stimulation is delivered with stimulation parameters configured to suppress ventricular tachyarrhythmia of the patient, wherein the stimulation parameters comprise a stimulation frequency less than or equal to 40 hertz (Hz).

22 Claims, 9 Drawing Sheets

(58) Field of Classification Search
CPC .............. A61N 1/3628; A61N 1/36114; A61N 1/36167; A61N 1/36171; A61N 1/36592; A61B 5/363
See application file for complete search history.

(56) References Cited

U.S. PATENT DOCUMENTS

| | | | |
|---|---|---|---|
| 8,880,170 | B2 | 11/2014 | Bradley et al. |
| 9,814,886 | B2 | 11/2017 | Zhou et al. |
| 2010/0094376 | A1* | 4/2010 | Penner ................. A61N 1/0517 607/42 |
| 2010/0114195 | A1 | 5/2010 | Burnes et al. |
| 2013/0289636 | A1 | 10/2013 | Karamanoglu et al. |
| 2014/0114385 | A1 | 4/2014 | Nijhuis et al. |
| 2022/0028060 | A1* | 1/2022 | Masuda ................. G16H 40/67 |

OTHER PUBLICATIONS

Crozier et al., "First-in-Human Chronic Implant Experience of the Substernal Extravascular Implantable Cardioverter-Defibrillator," JACC Clinical Electrophysiology, vol. 6, No. 12, Aug. 2020, 12 pp.

Gardner et al., "Dependence of Non-Adrenergic Inhibition of Cardiac Vagal Action on Peak Frequency of Sympathetic Stimulation in the Dog," Journal of Physiology, vol. 405, Nov. 1988, pp. 115-122.

Goldstein et al., "LF Power of Heart Rate Variability is not a Measure of Cardiac Sympathetic Tone but may be a Measure of Modulation of Cardiac Autonomic Outflows by Baroreflexes," Experimental Physiology, vol. 96, No. 12, Dec. 2011, pp. 1255-1261.

Kornet et al., "Stimulation of the Intra-Cardiac Vagal Nerves Innervating the AV-Node to Control Ventricular Rate During AF: Specificity, Parameter Optimization and Chronic use up to 3 Months," Journal of Interventional Cardiac Electrophysiology, vol. 33, No. 1, Jan. 2011, pp. 7-18.

Malliani et al., "Cardiovascular Neural Regulation Explored in the Frequency Domain," Circulation, vol. 84, No. 2, Aug. 1991, pp. 482-492.

Neukirchen et al., "Sympathetic Nervous System: Evaluation and Importance for Clinical General Anesthesia," Anesthesiology, vol. 109, No. 6, Dec. 2008, pp. 1113-1131.

Oliveira et al., "Acute Vagal Modulation of Electrophysiology of the Atrial and Pulmonary Veins Increases Vulnerability to Atrial Fibrillation," Experimental Physiology, vol. 96, No. 2, Feb. 2011, pp. 125-133.

Quan et al., "Endocardial Stimulation of Efferent Parasympathetic Nerves to the Atrioventricular Node in Humans: Optimal Stimulation Sites and the Effects of Digoxin," Journal of Interventional Cardiac Electrophysiology, vol. 5, Jun. 2001, pp. 145-152.

Stein et al., "Transcutaneous Electrical Nerve Stimulation at Different Frequencies on Heart Rate Variability in Healthy Subjects," Autonomic Neuroscience: Basic and Clinical, vol. 165, No. 2, Dec. 7, 2011, pp. 205-208.

Tran et al., "Inhibitory Effect of Neuropeptide Y on Adrenergic and Cholinergic Transmission in Rat Urinary Bladder and Urethra," American Journal of Physiology, vol. 266, No. 4, Apr. 1994, pp. 1411-1417.

U.S. Appl. No. 17/649,615, filed Feb. 1, 2022, naming inventors Hernandez et al.

Vanoli et al., "Vagal Stimulation and Prevention of Sudden Death in Conscious Dogs With a Healed Myocardial Infarction," Circulation Research, vol. 68, No. 5, May 1991, pp. 1471-1481.

\* cited by examiner

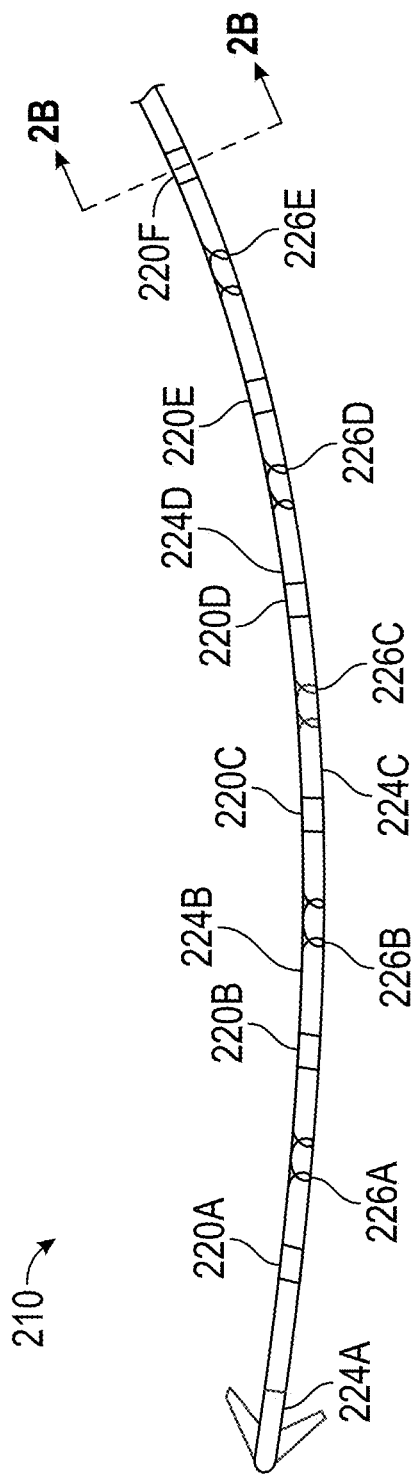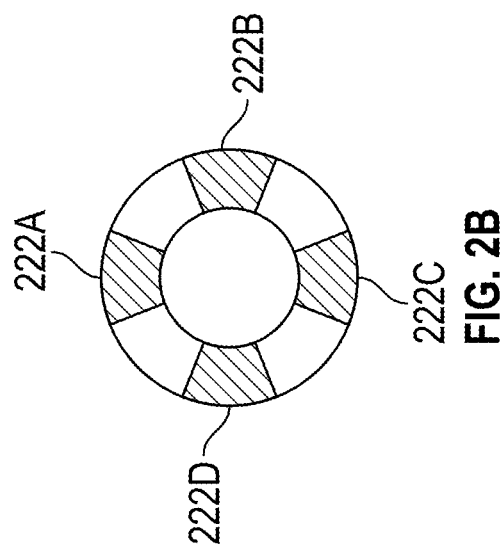
FIG. 2A
FIG. 2B

INHIBITION OF ONSET OF CARDIAC TACHYARRHYTHMIA WITH INTERCOSTAL NERVE STIMULATION This application claims the benefit of U.S. Provisional Application Ser. No. 63/188,278, filed May 13, 2021, the entire content of which is incorporated herein by reference.

TECHNICAL FIELD

This disclosure generally relates to medical devices and, more particularly, medical devices for monitoring and/or treating cardiac conditions.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of ventricular fibrillation, the use of an implantable cardioverter defibrillator (ICD) system has been shown to be beneficial at preventing SCD. An ICD system includes an ICD that is a battery powered electrical shock device, that may include an electrical housing electrode (sometimes referred to as a can electrode), and that is typically coupled to one or more electrical leads placed within the heart. If an arrhythmia is sensed, the ICD may send a pulse via a combination of electrodes on the electrical leads and/or housing to shock the heart and restore its normal rhythm. Owing to the inherent surgical risks in attaching and replacing electrical leads directly within or on the heart, extracardiovascular or extracardiac ICD systems have been devised to provide shocks to the heart without placing electrical leads within the heart or attaching electrical leads directly to the heart.

Some tachyarrhythmias may be terminated by anti-tachycardia pacing (ATP) therapy. ICDs have been configured to attempt to terminate some detected tachyarrhythmias by delivery of ATP prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

SUMMARY

In general, the disclosure describes a medical device to assist in inhibition of, e.g., prevention of, the onset of ventricular tachyarrhythmias. More particularly, the medical device may be configured to deliver electrical stimulation to an intercostal nerve of a patient with stimulation parameters configured to inhibit ventricular tachyarrhythmia. In some examples, the stimulation parameters comprise a stimulation frequency of 40 hertz (40 Hz) or less.

The medical device may monitor one or more predictive markers for upcoming tachyarrhythmias or other deterioration of the heart status. An example of a predictive marker is heartbeat variability. If the predictive marker(s) satisfy a threshold or other criterion, the medical device may deliver neurostimulation to the intercostal nerve. In some examples, the medical device delivers the neurostimulation until the predictive marker(s) no longer satisfy the criterion, e.g., move back to a normal range, or a certain time elapses. The medical device may store physiological data resulting in satisfaction of the predictive marker(s), stimulation parameters and outcomes, and may finetune the stimulation parameters based on the outcomes. In some examples, in the event that a tachyarrhythmia is detected during delivery of the electrical stimulation, the medical device will stop delivery of the electrical stimulation, and deliver defibrillation therapy or another anti-tachyarrhythmia therapy.

The medical device may be configured to position one or more electrodes proximate to an intercostal nerve. In some examples, the medical device may be implanted, and the electrode may be positioned in the intercostal space between the second and third or the third and fourth ribs, on either or both of the right or left side of the patient. In some examples, the medical device is configured to be implanted in or over the intercostal space, and may optionally include a lead configured to extend in the intercostal space to position the electrode proximate to the intercostal nerve.

In some examples, a medical device is configured to provide both ICD and neurostimulator functionality. In some of these examples, an implantable lead coupled to the ICD is configured to position one or more electrodes extravascularly in the substernal or subcutaneous space close to the heart. These electrodes may reach the cardiac vicinity to sense, stimulate and shock the heart. The lead may additionally be configured to position one or more electrodes proximate to the intercostal nerve for delivery of electrical stimulation to the intercostal nerve. In such examples, the medical device may detect triggers that initiate cardiac tachyarrhythmias based on one or more predictive markers, and, when the triggers are detected, deliver the electrical stimulation to the intercostal nerve to inhibit cardiac tachyarrhythmias. In such examples, the implantable medical device may be further configured to treat cardiac tachyarrhythmias in case prevention of the tachyarrhythmia is ineffective. The medical device may combine intercostal stimulation with an extravascular ICD to prevent the occurrence of ventricular arrhythmias, and if this is not possible, to have fallback options with ATP, cardioversion, and defibrillation shocks.

In one example, this disclosure describes a medical device includes a plurality of electrodes; therapy delivery circuitry; and processing circuitry configured to control the therapy delivery circuitry to deliver electrical stimulation to an intercostal nerve of a patient via at least two of the plurality of electrodes, wherein the electrical stimulation is delivered with stimulation parameters configured to suppress ventricular tachyarrhythmia of the patient, wherein the stimulation parameters comprise a stimulation frequency of 40 hertz (Hz) or less.

In another example, this disclosure describes a method includes delivering electrical stimulation, by therapy delivery circuitry of a medical device further comprising processing circuitry and a plurality of electrodes, to an intercostal nerve of a patient via at least two of the plurality of electrodes; wherein delivering the electrical stimulation includes delivering with stimulation parameters configured to suppress ventricular tachyarrhythmia of the patient, wherein the stimulation parameters comprise a stimulation frequency less than or equal to 40 hertz (Hz).

In another example, this disclosure describes a computer-readable storage medium comprising instructions that, when executed by processing circuitry of a medical device comprising a plurality of electrodes, cause the medical device to:

deliver electrical stimulation to an intercostal nerve of a patient via at least two of the plurality electrodes; wherein the electrical stimulation is delivered with stimulation parameters configured to suppress ventricular tachyarrhythmia of the patient, wherein the stimulation parameters comprise a stimulation frequency less than or equal to 40 hertz (Hz).

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 2A is a side view of a portion of a lead for the example medical device system according to the techniques of the disclosure.

FIG. 2B is a cross-sectional view of a portion of the lead of FIG. 2A taken along 2B-2B.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1:
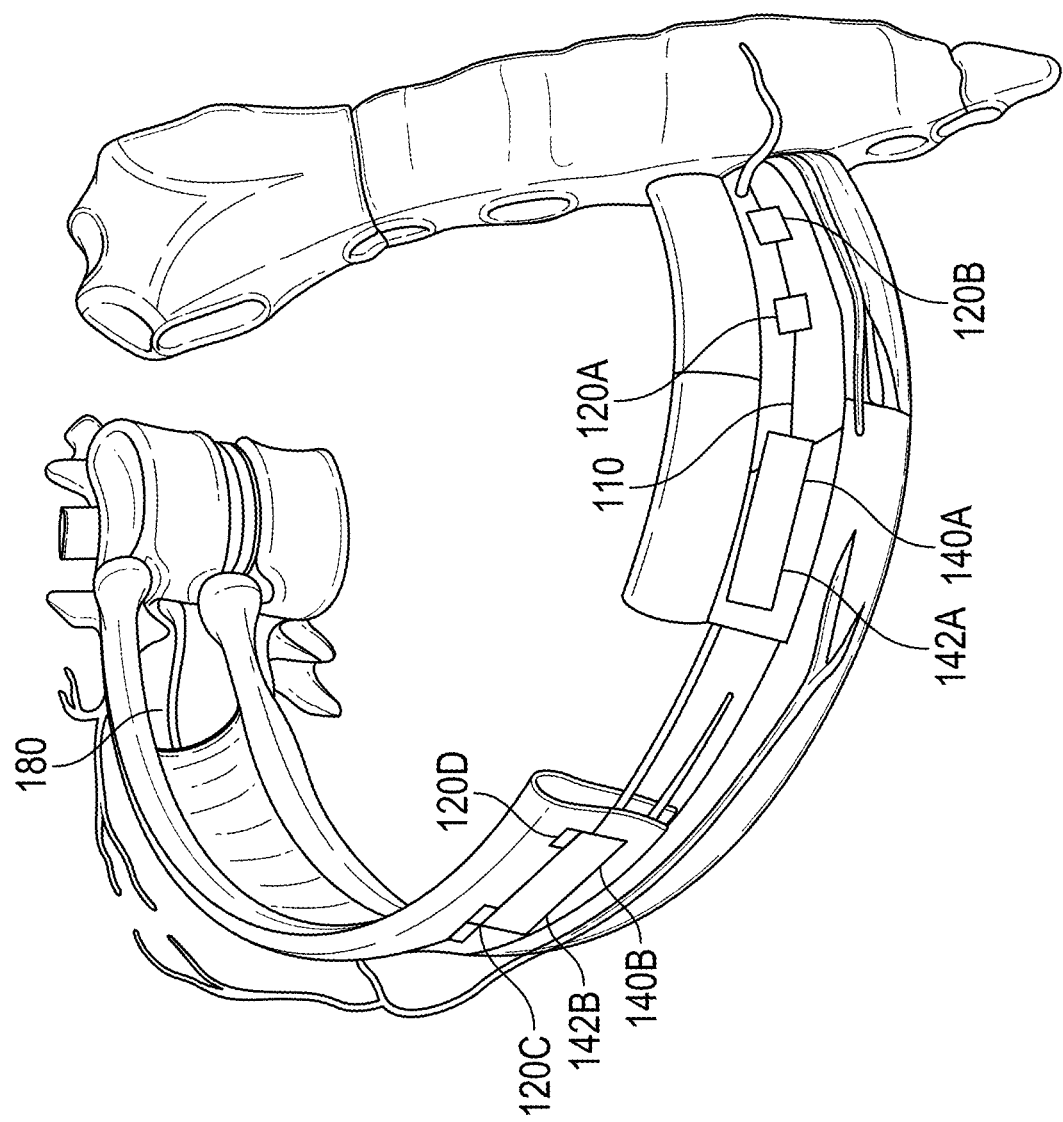
FIG. 1 is a perspective view of an example medical device system in conjunction with a patient according to the techniques of the disclosure.

FIG. 1 is a perspective view of two example medical devices 140A and 140B (collectively "medical devices 140") in conjunction with the intercostal anatomy of a patient. Although two medical devices 140 are shown in FIG. 1 for purposes of illustration, a patient may be implanted with one medical device 140, or more than two medical devices 140, in some examples. Although illustrated as implanted on the right side of the patient, one or more medical devices 140 may additionally or alternatively be implanted on the left side of the patient.

Medical devices 140 are configured to deliver electrical stimulation to intercostal nerve 180. Medical device(s) 140 may transmit data to and receive programming instructions from an external device (not shown). According to the techniques of the disclosure, medical device(s) 140 may detect one or more cardiac signals to determine if a heartbeat variability metric has been satisfied and, based on satisfaction of the metric, deliver electrical stimulation therapy to an intercostal nerve to inhibit tachyarrhythmia.

Medical device(s) 140 may be implanted subcutaneously or sub-muscularly on the thorax of the patient proximate to the target intercostal nerve 180. Electrodes of medical devices 140 are positioned to sense a patient's heart of patient, and stimulate intercostal nerve 180 in the intercostal space, in some examples between ribs 2 and 3. In some examples, the electrodes of a medical device 140 may be configured to electrically stimulate the intercostal nerve 180 in the intercostal space between ribs 3 and 4, and may be on either the right or left side of a patient.

In some examples, medical device 140A may include a lead 110 extending from a stimulator 142, where the lead 110 includes one or more electrodes 120A, 120B. In some examples, medical devices 140 may be placed subcutaneously in intercostal space. In some examples, at least a portion of medical devices 140, e.g., of lead 110 of medical device 140A, may be disposed in a facial plane adjacent the intercostal nerve 180. In some examples in which stimulator 142A includes one or more electrodes, e.g., a housing of stimulator 142 acts as an electrode, the lead 110 may provide additional electrodes to stimulator 142. In some examples, medical device 140B is leadless and includes a plurality of electrodes 120C, 120D on or integral with a housing of stimulator 142B. In one or more examples, stimulating current may pass from the electrodes 120C, 120D though intercostal space and may activate muscles in addition to intercostal nerve 180.

In the example of FIG. 1, medical devices 140 may be configured to sense electrical activity of a heart and deliver electrical stimulation therapy, e.g., therapy to suppress ventricular tachyarrhythmia, to intercostal nerve 180 of a patient via at least two of the plurality of electrodes 120A, 120B, 120C, 120D. In some examples, medical device 140A senses electrical signals using the electrodes 120A, 120B carried on the lead 110. In some examples, medical device 140B senses electrical cardiac signals using the electrodes 120C, 120D carried on the housing of ICD 140B. These electrical signals may be electrical signals generated by cardiac muscle and indicative of depolarizations and repolarizations of a patient's heart at various times during the cardiac cycle. Medical devices 140 may analyze the sensed electrical signals to determine a heartbeat variability metric based on the cardiac signal, and may control delivery of electrical stimulation to intercostal nerve 180 based on the heartbeat variability metric.

Stimulators 142A, 142B of medical devices 140A, 140B may include a housing that forms a hermetic seal that protects components of the medical devices. The housings of medical devices 140 may be formed of a conductive material, such as titanium or titanium alloy, which may function as a housing electrode (sometimes referred to as a can electrode). As will be described in further detail herein, each of the housings may house one or more processors, memories, transmitters, receivers, sensors, sensing circuitry, therapy circuitry, power sources, and other appropriate components. The housings are configured to be implanted in a patient.

FIGS. 2A and 2B respectively illustrate a perspective and cross-section view of a portion of an example lead 210 that may be incorporated with a medical device 140. In some examples, lead 210 may include one or more anchor tines such as tines 224A, 224B, 224C, 224D, and 224E (collectively, "tines 224") as shown in FIG. 2A, where tine 224A may be disposed at a distal end of the lead, for example. In some examples, one or more of tines 224 may include small projections coupled to lead body and extending away from the lead body, for example, at an acute angle. One or more of tines 224 may assist in anchoring lead 210 within an intercostal space of a patient, e.g., by interacting with muscle and or facia in the intercostal space. In some examples, leads may include tines configured differently than those illustrated in FIGS. 2A and 2B. In some examples, leads may additionally or alternatively include fixation mechanisms other than tines, such as helical fixation mechanism, or balloons or other expandable fixation mechanisms.

In one or more examples, lead 210 may include a plurality of electrodes, such as one or more of electrodes 220A, 220B, 220C, 220D, 220E, and 220F (collectively "electrodes 220"). In one or more examples, one or more of electrodes 220 may include segmented electrodes. For example, as shown in FIG. 2B, electrode 220F may include four segmented electrodes 222A, 222B, 222C, and 222D at different angular positions (in the case of lead 210 with a circular cross-section, the angular position may be referred to as a circumferential position) around lead 210. In one or more examples, one or more of electrodes 220 may be spaced over 10-30 centimeters (cm) of a lead length to assist in stimulating all or most of an intercostal nerve. In some examples, the lead 210 may include one or more springs 226A, 226B, 226C, 226D, and 226E or other elements to provide flexibility to lead 210 and allow lead 210 to confirm to the ribs or other anatomy of the patient. In some examples, lead 210 additionally or alternatively includes coiled conductors that extend through one or more lumen defined by lead 210 to couple electrodes 220 to electrical contacts at the proximal end of lead 210 (not shown), which may provide flexibility to lead 210 and allow lead 210 to confirm to the ribs or other anatomy of the patient.

Lead 210, e.g., in examples in which one or more electrodes 220 are configured as segmented electrodes, may also be described as including a complex electrode array geometry. A complex electrode array geometry may be an electrode array that includes at least one level of segmented electrodes (e.g., circumferentially positioned electrodes). In another example, a complex electrode array geometry may refer to an electrode array that includes electrodes centered in two, three, or even more planes. A complex electrode geometry may indicate any electrode array in which different electrode combinations may be used to deliver electrical stimulation in multiple directions (e.g., radial directions) away from the lead. Thus, the complex electrode array geometry may include multiple levels of segmented ring electrodes, segmented ring electrodes and ring electrodes, or any other combination of electrodes including at least one level of segmented ring electrodes. Segmented ring electrodes may generally be two or more electrodes located at different angular or circumferential positions around the circumference of lead body. Segmented ring electrodes or other complex electrode array geometries may be used to produce customizable stimulation fields (e.g., electrical fields that may affect or activate patient tissue) that may be directed to a particular side of lead 210 in order to isolate the stimulation field around the target anatomical region. In the example of FIGS. 2A and 2B, a complex electrode array geometry of lead 210 may facilitate use of certain segmented electrodes 222 for delivery of electrical stimulation to intercostal nerve 180, e.g., while avoiding stimulation of other tissues, and other segmented electrodes 222 for sensing cardiac activity.

Figure 3A:
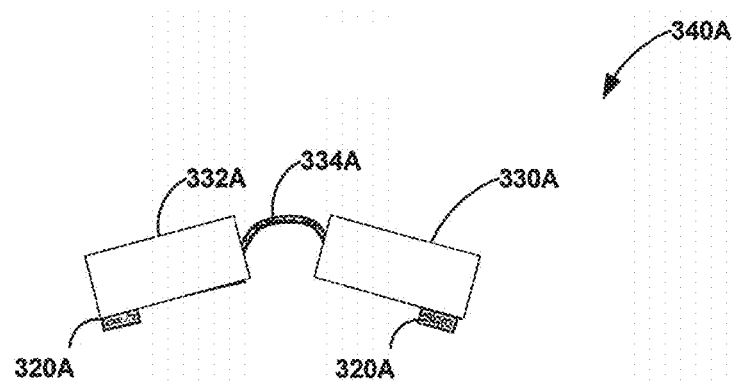
FIG. 3A is a side view of an example medical device system according to the techniques of the disclosure.
Figure 3B:
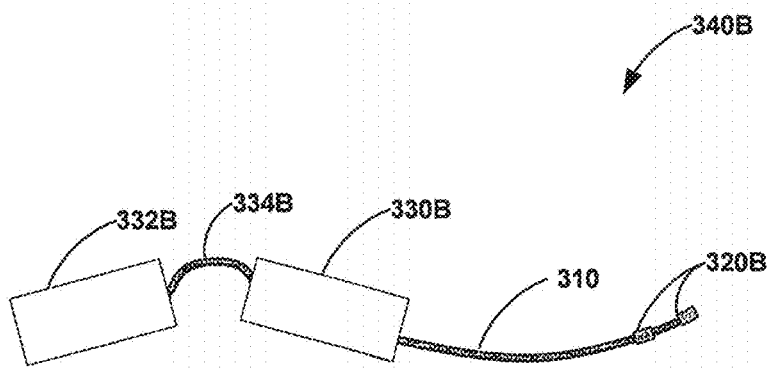
FIG. 3B is a side view of an example medical device system according to the techniques of the disclosure.

FIGS. 3A and 3B respectively illustrate other example medical devices 340A and 340B (collectively "medical devices 340"). Medical device 340A includes an electronics module 330A connected to a battery 332A by a flexible connector 334A. Similarly, medical device 340B includes an electronics module 330B connected to a battery 332B by a flexible connector 334B. Medical device 340B also includes a lead 310 connected to electronics module 330B. Each of electronics modules 330A, 330B and batteries 332A, 332B may include a housing substantially similar to that described above with respect to stimulators 142 (FIG. 1). Flexible connectors 334A, 334B may be a flex circuit or any other configuration of one or more electrically-insulated conductors configured to electrically connect the electronics modules to the batteries.

Medical devices 340 differ from medical devices 140 (FIG. 1) in that the electronic components of the medical device (e.g., one or more processors, memories, transmitters, receivers, sensors, sensing circuitry, therapy circuitry, and power sources) are distributed within two or more flexibly-connected housings, rather than a single stimulator 142 housing as illustrated in FIG. 1. Distributing the volume of the components amongst multiple flexibly-connected housings may allow medical devices 340 as a whole to be smaller in one or more dimensions, e.g., have a lower height or profile above the ribs, and to better conform to the ribs. In the examples illustrated by FIGS. 3A and 3B, the batteries 332A, 332B are separated from the remainder of the components, but other divisions of components are possible in other examples.

In some examples, medical devices 340 have a volume of about 1 cubic centimeter (cc). Batteries 332A, 332B may be primary or rechargeable batteries. In some examples, the medical device 340A may be formed to have or may include one or more electrodes 320A on the outermost portion of the housing 330A and/or the battery 332A. In some examples, medical device 340B may include a lead 310 extending from housing 330, where the lead 310 may include one or more electrodes 320B thereon. The electrodes 320A, 320B of medical devices 340A, 340B may be disposed proximate to the intercostal nerve, for example, as shown in FIG. 1. In one or more examples, wherein at least one of the plurality of electrodes comprises a sensing electrode, and the housing is configured together with the cardiac sensing electrode to sense a cardiac signal.

Figure 4:
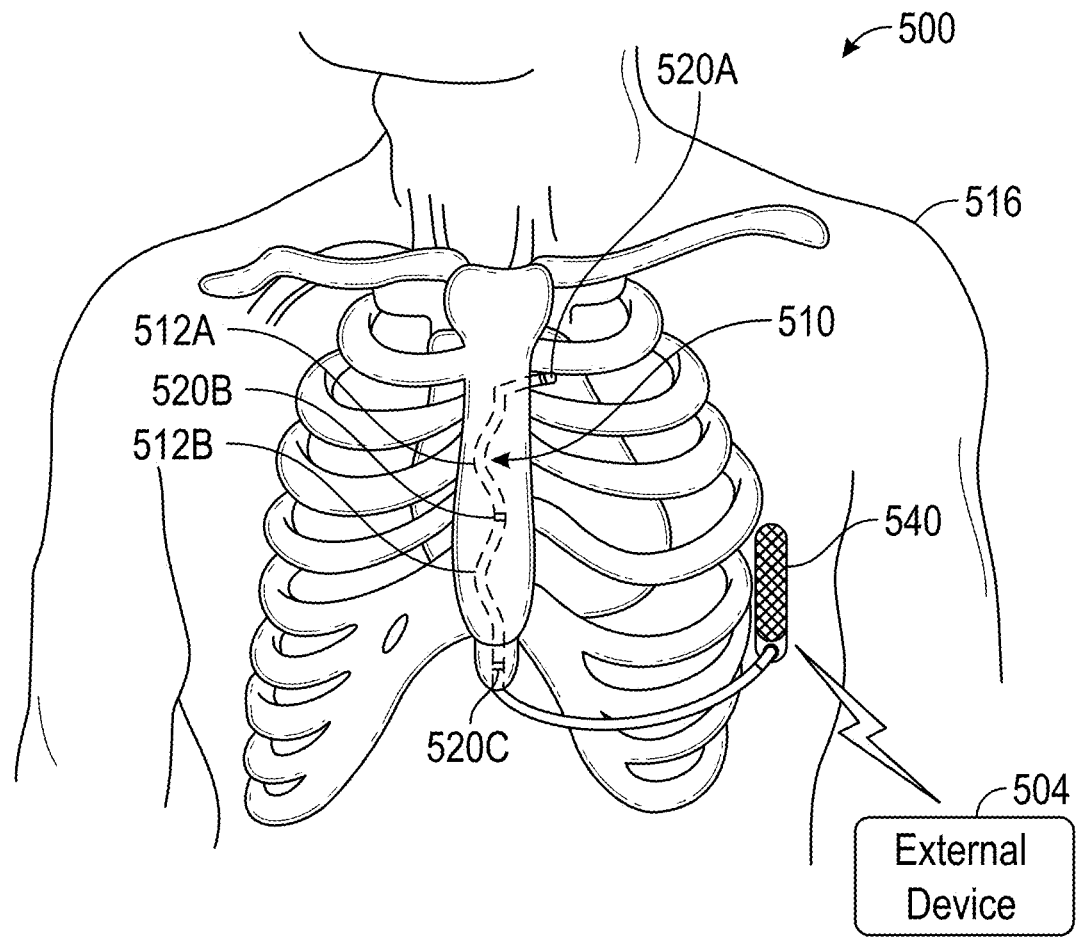
FIG. 4 is a front view of an example medical device system in conjunction with a patient according to the techniques of the disclosure.
Figure 5:
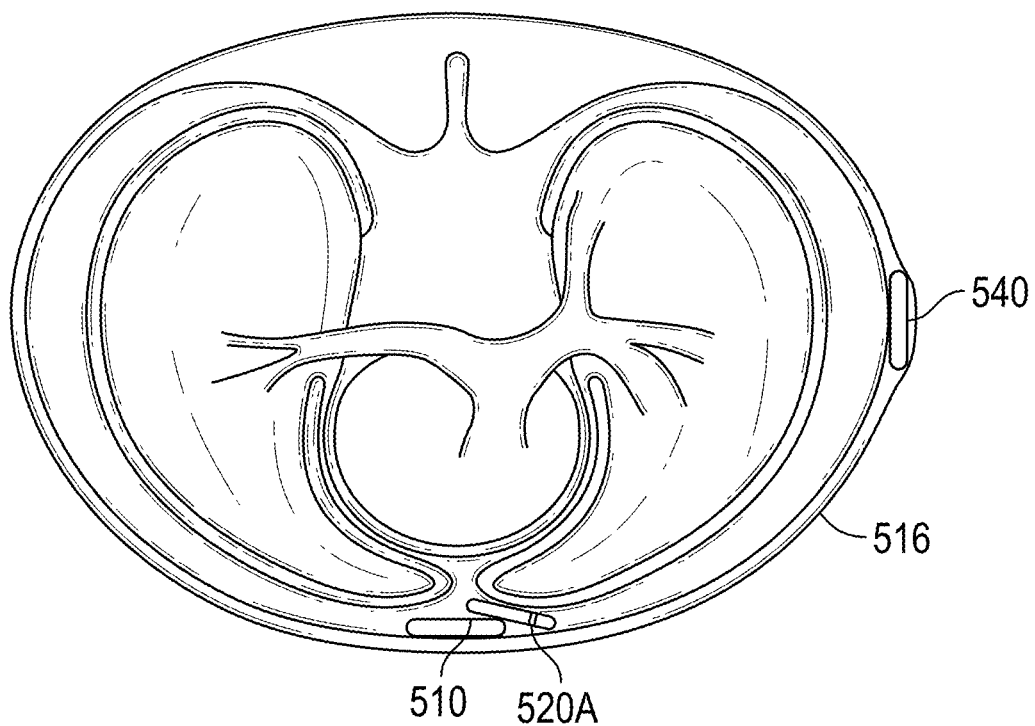
FIG. 5 is a transverse view of the example medical device system in conjunction with the patient according to the techniques of the disclosure.

FIGS. 4 and 5 illustrate an example medical device 500 implanted within a patient 516. Medical device 500 provides cardiac therapy to the heart of the patient. In the example illustrated by FIGS. 4 and 5, medical device 500 is configured as an extracardiovascular ICD system. Medical device 500 may include an ICD 540 connected to an extravascular medical electrical lead 510. Lead 510 may include any of leads 610A, 610B of FIGS. 6A, 6B, for example. Medical device 500 may transmit data to and receive programming instructions from an external device 504. According to the techniques of the disclosure, medical device 500 may detect one or more cardiac signals to determine if a heartbeat variability metric has been satisfied and detect tachyarrhythmias, delivers therapy to an intercostal nerve based on satisfaction of the heartbeat variability metric to inhibit tachyarrhythmia prior to its occurrence, and may deliver defibrillation or other antitachyarrhythmia therapy in response to detecting a tachyarrhythmia.

Medical device 500, e.g., lead 510, is implanted extravascularly in a substernal or subcutaneous space close to a patient's heart. Electrodes 512A, 512B, 520A, 520B, 520C of medical device 500 electrically reach a cardiac vicinity to sense, stimulate and shock a patient's heart, as well as stimulate an intercostal nerve in the intercostal space, in some examples between ribs 2 and 3. In some examples, the electrodes of medical device 500 electrically stimulate the intercostal nerve 180 in the intercostal space between ribs 3 and 4, and on either or both of the right or left side of a patient. In the example of FIGS. 4 and 5, a distal portion of lead 510 including electrode 520A extends laterally from a substernal position to position electrode 520A proximate to an intercostal nerve. ICD 540 may use electrode 520A in combination with any of the other electrodes and/or a housing of ICD 540 to deliver the electrical stimulation to the intercostal nerve. In some examples, two or more electrodes on a distal portion of lead 510 may be positioned proximate to an intercostal nerve for delivery of electrical stimulation to the intercostal nerve. In some examples, the distal portion of lead 510 including electrode 520A may be disposed in a facial plane adjacent the intercostal nerve.

In some examples, medical device 500 senses electrical signals, e.g., cardiac electrical signals, using the any combination of two or more of the electrodes carried on the lead 510 and/or on a housing of ICD 540. ICD 540 may analyze the sensed electrical signals to determine a heartbeat variability metric, and may deliver electrical stimulation to the intercostal nerve via lead 510 based on the heartbeat variability metric. In some examples, ICD 540 may detect tachyarrhythmias based on the sensed signals, such as ventricular tachycardia or ventricular fibrillation. In response to detecting tachyarrhythmia, ICD 540 may, e.g., depending on the type of tachyarrhythmia, deliver therapy via the electrodes 512A, 512B to terminate the tachyarrhythmia, such as defibrillation or other antitachyarrhythmia shocks. In some examples, electrodes 512A, 512B may be referred to as defibrillation electrodes, although they may be used for cardiac sensing or to deliver any therapy described herein, and may be configured as coils. In some examples, ICD 540 may deliver anti-tachycardia pacing (ATP) via one or both of electrodes 520B and 520C in response to detecting a tachyarrhythmia. In some examples, ICD 540 delivers other types of cardiac pacing, such as a bradycardia pacing, post-shock pacing, or cardiac resynchronization therapy (CRT).

ICD 540 may include a housing that forms a hermetic seal that protects components of the ICD 540. The housing of the ICD 540 may be formed of a conductive material, such as titanium or titanium alloy, which may function as a housing electrode (sometimes referred to as a can electrode). As will be described in further detail herein, housing may house one or more processors, memories, transmitters, receivers, sensors, sensing circuitry, therapy circuitry, power sources, and other appropriate components. The housing is configured to be implanted in a patient.

Figure 6A:
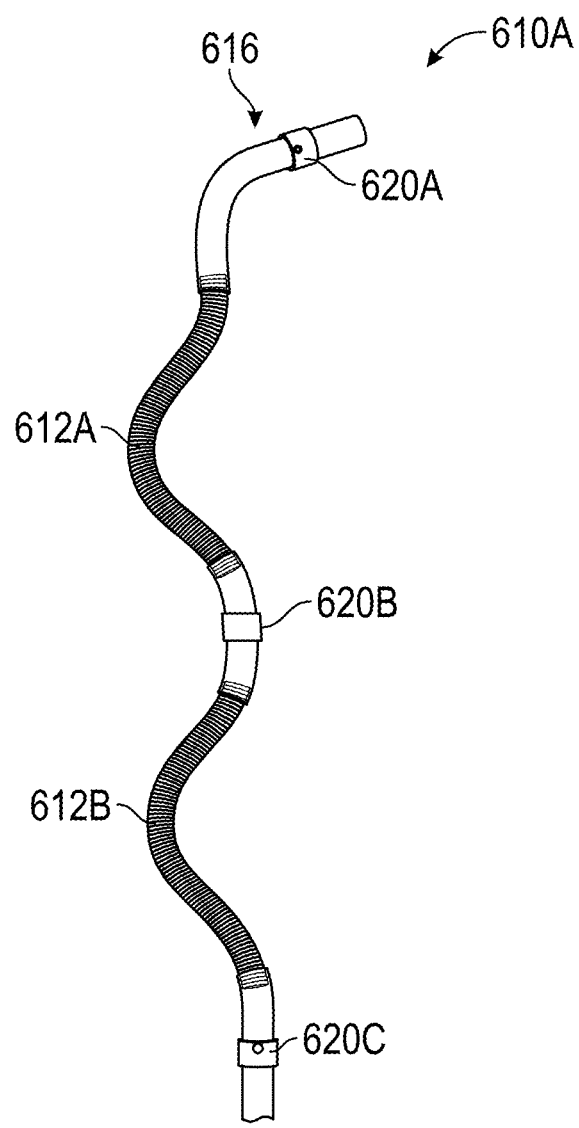
FIG. 6A is a side view of a portion of a lead for the example medical device system according to the techniques of the disclosure.
Figure 6B:
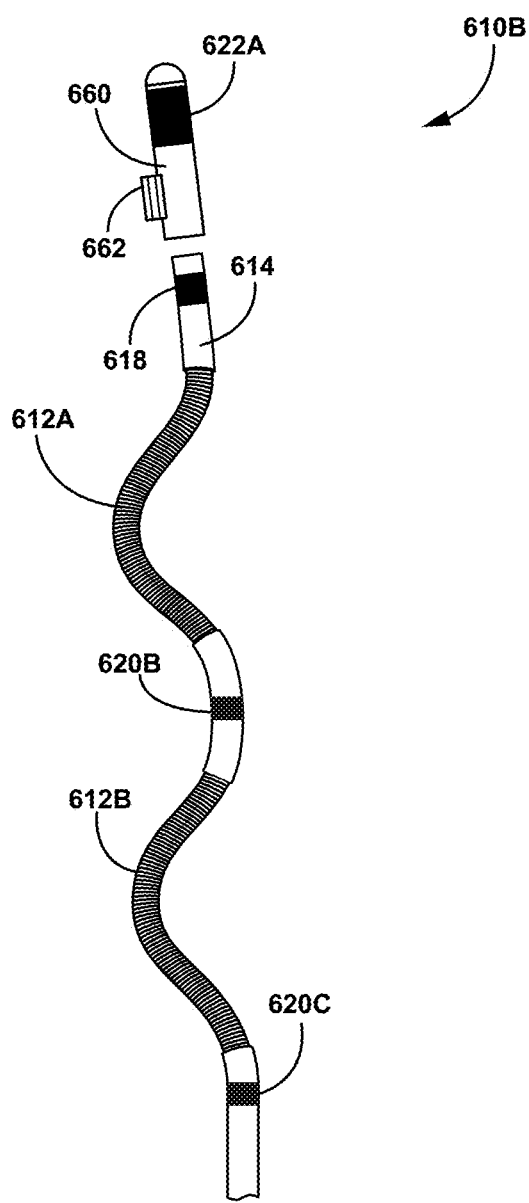
FIG. 6B is a side view of a portion of a lead for the example medical device system according to the techniques of the disclosure.

FIGS. 6A and 6B illustrate example leads 610A, 610B (collectively referred to as "leads 610") for use with the medical device 500 shown in FIGS. 4-5. Leads 610 may be example configurations of lead 510 illustrated in FIGS. 4-5. Leads 610 include a plurality of electrodes 612A, 612B, and 620A-620C, which may be configured to deliver therapy and/or sense signals as described above with respect to electrodes 512A, 512B, and 520A-520C of lead 510.

Like lead 510 illustrated in FIGS. 4 and 5, distal portions of leads 610 including electrode 620A extend laterally from a substernal position to position one or more electrodes, e.g., electrode 620A, proximate to an intercostal nerve. In some examples, as shown in FIG. 6A, distal portion 616 is an integral portion of a unitary body of lead 610A. In some examples, as shown in FIG. 6B, lead 610B may include a distal end 614 that may be configured to receive an extension 660 thereon, or otherwise be connected to extension 660. Extension 660 includes one or more electrodes, e.g., electrode 622A, configured for stimulating an intercostal nerve. Extension 660 may be used to ensure an end of the lead 610B including electrode 620A is disposed in close proximity to a rim of the sternum approximately at the intercostal space between rib 2 and rib 3, for example.

Distal end 614 may include an electrical contact 618 that may be electrically connected to electrode 620A when extension 660 is received on distal end 614. In this manner, ICD 540 may sense electrical signals and deliver electrical therapy via electrode 620A. In some examples, contact 618 may be an electrode, and the use extension 660 may allow lead 610B to be modified for delivery of electrical stimulation to an intercostal nerve as described herein.

In the example of FIG. 6B, extension 660 includes a side rail 662 that may be used for placement of extension 660 during implantation, e.g., over a guidewire. In some examples, side rail 662 may also be configured for orientation and fixation of extension 660 within patient tissue. Extension 660 may additionally or alternatively include various other fixations mechanisms, such as tines, hooks, barbs, or balloons.

Electrodes 620A-620C of leads 610 may also be described as including a complex electrode array geometry. A complex electrode array geometry may be an electrode array that includes at least one level of segmented ring electrodes (e.g., circumferentially positioned electrodes). In another example, a complex electrode array geometry may refer to an electrode array that includes electrodes centered in two, three, or even more planes. A complex electrode geometry may indicate any electrode array in which different electrode combinations may be used to deliver electrical stimulation in multiple directions away from the lead. Thus, the complex electrode array geometry may include multiple levels of segmented ring electrodes, segmented ring electrodes and ring electrodes, or any other combination of electrodes including at least one level of segmented ring electrodes. Segmented ring electrodes may generally be two or more electrodes located at different angular or circumferential positions around the circumference of lead body. Segmented ring electrodes or other complex electrode array geometries may be used to produce customizable stimulation fields (e.g., electrical fields that may affect or activate patient tissue) that may be directed to a particular side of lead in order to isolate the stimulation field around the target anatomical region.

Figure 7:
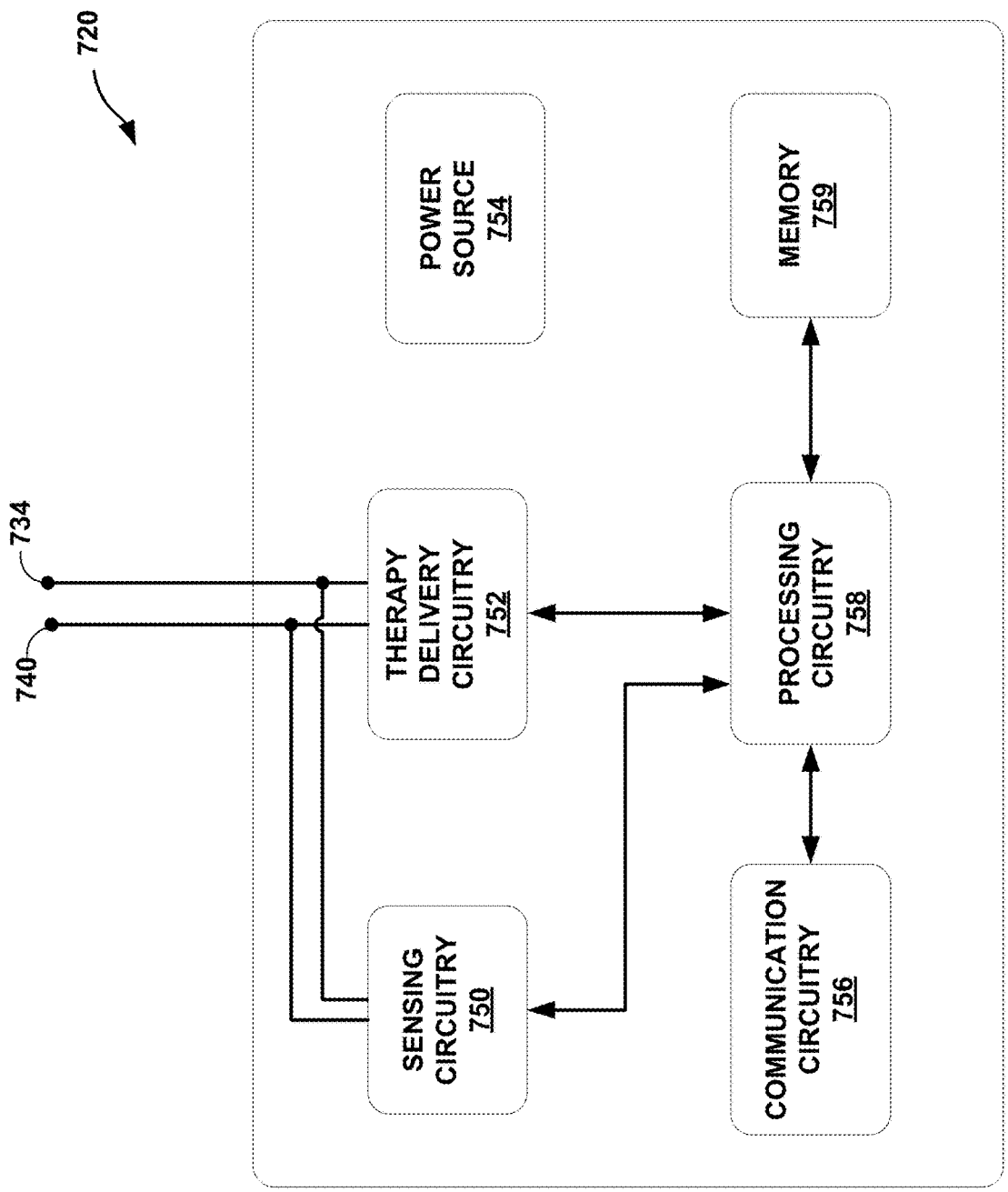
FIG. 7 is a block diagram of an example medical device system according to the techniques of the disclosure.

FIG. 7 is a block diagram of an example configuration of a medical device 720, which may correspond to any of medical devices 140 or 500 in FIG. 1 or 4, according to the techniques of the disclosure. In the illustrated example, medical device 720 includes processing circuitry 758, memory 759, communication circuitry 756, sensing circuitry 750, therapy delivery circuitry 752, and power source 754. Memory 759 includes computer-readable instructions that, when executed by processing circuitry 758, cause medical device 720 and processing circuitry 758 to perform various functions attributed to medical device 720 and processing circuitry 758 herein (e.g., sensing cardiac signals, determining heart beat variability metrics, delivering intercostal nerve stimulation, detecting tachyarrhythmias, and delivering antitachyarrhythmia therapies). Memory 759 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 758 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 758 may include multiple components, such as any combination of one or more microprocessors, one or more controllers, one or more DSPs, one or more ASICs, or one or more FPGAs, as well as other discrete or integrated logic circuitry. The functions attributed to processing circuitry 758 herein may be embodied as software, firmware, hardware or any combination thereof.

Processing circuitry 758 controls therapy delivery circuitry 752 to deliver stimulation therapy to an intercostal nerve, and in some examples deliver stimulation or other electrical therapy to a heart, according to therapy parameters, which may be stored in memory 759. For example, processing circuitry 758 may control therapy delivery circuitry 752 to deliver electrical pulses with the amplitudes, pulse widths, frequency, or electrode polarities specified by the therapy parameters. In this manner, therapy delivery circuitry 752 may deliver neurostimulation pulses to an intercostal nerve via electrodes 734 and 740. In some examples, therapy delivery circuitry 752 may deliver the stimulation in the form of voltage or current electrical pulses. In other examples, therapy delivery circuitry 752 may deliver one or more of these types of stimulation in the form of other signals, such as sine waves, square waves, or other substantially continuous time signals. In some examples, processing circuitry 758 controls therapy delivery circuitry 752 to deliver therapy to the heart as described herein, such as cardiac pacing and/or defibrillation shocks.

Therapy delivery circuitry 752 is electrically coupled to electrodes 734 and 740 carried on the housing or a lead of medical device 720. Although medical device 720 may only include two electrodes, e.g., electrodes 734 and 740, in other examples, medical device 720 may utilize three or more electrodes. Electrodes 734 and 740 may correspond to any of electrodes 120, 220, 320, 512, 520, 612, or 620 described herein. ICD 720 may use any combination of electrodes to deliver therapy to and/or detect electrical signals from patient. In some examples, therapy delivery circuitry 752 includes a charging circuit, one or more pulse generators, capacitors, transformers, switching modules, and/or other components capable of generating and/or storing energy to deliver as neurostimulation therapy, cardiac pacing therapy, or antitachyarrhythmia shock therapy. In some examples, therapy delivery circuitry 752 delivers therapy as one or more electrical pulses according to one or more therapy parameter sets defining a voltage or current amplitude, a frequency, a pulse width, a duty cycle, or other parameters of the therapy.

Sensing circuitry 750 monitors signals from electrodes 734 and 740 in order to monitor electrical activity of a patient's heart, e.g., a cardiac electrogram (EGM), impedance, or other electrical phenomenon. In some examples, sensing circuitry 750 includes one or more analog components, digital components or a combination thereof. In some examples, sensing circuitry 750 includes one or more sense amplifiers, comparators, filters, rectifiers, threshold detectors, analog-to-digital converters (ADCs) or the like. In some examples, sensing circuitry 750 converts sensed signals to digital form and provides the digital signals to processing circuitry 758 for processing or analysis. In one example, sensing circuitry 750 amplifies signals from electrodes 734 and 740 and converts the amplified signals to multi-bit digital signals by an ADC.

In some examples, sensing circuitry 750 performs sensing to determine heart signals, heart rates or heart rate variability, detect arrhythmias (e.g., tachyarrhythmias or bradycardia), or to measure morphological features or intervals between features of the signals.

In some examples, processing circuitry 758 may determine a heartbeat variability metric or cardiac metric, where the heartbeat variability metric or cardiac metric may be based on the cardiac signal. In some examples, the cardiac signal may include T-wave related changes, i.e., indices of dispersion of repolarization like QTV. In some examples, the cardiac signal may include QTc, ST interval, ST elevation, T wave amplitude, T peak to T end, T slope, T-wave area, T-wave asymmetry, R-wave/T-wave amplitude, and/or the variabilities of these parameters as well as T-wave alternans by beat to beat envelop analyses or autonomic markers such as heart rate variability related markers in the time and frequency domain, heart rate turbulence onset and slope and deceleration capacity. In some examples, processing circuitry 758 may include a machine learning algorithm that optimizes a weight of the various metrics and/or cardiac signals to determine a representative threshold for an imminent ventricular arrhythmia. In one or more examples, the machine learning algorithm may optimize the weight of these parameters to determine the representative threshold for an imminent ventricular arrhythmia and where the parameters are corrected for one or more of the following activity level: medication, respiration level, heart rate, age, gender, weight, ST segment changes, time of the day (nocturnal, diurnal), comorbidities or disease progression, having diabetes 1 or 2.

In some examples, the heartbeat variability metric may include a T-wave alternans metric. In some examples, the heartbeat variability metric may include a heart rate variability metric. In some examples, the heartbeat variability metric may include a heart rate turbulence metric. In some examples, the heartbeat variability metric may include a QT interval variability metric. In some examples, the heartbeat variability metric may include a short term variability metric, such as a dispersion of QT intervals, or any other metric described in commonly-assigned U.S. patent application Ser. No. 17/649,615, titled "Short-Term Variability Sensing to Anticipate Tachyarrhythmias," filed Feb. 1, 2022, the entire content of which is incorporated herein by reference. In some examples, the cardiac metric may predict an oncoming VF with atrial fibrillation (AF) or QRS width, for example.

Once the heartbeat variability metric has been determined, processing circuitry 758 may control therapy delivery circuitry 752 to deliver electrical stimulation to the intercostal nerve of a patient based on satisfaction of a criterion by the metric. For example, the heartbeat variability metric may have one or more thresholds associated therewith.

For example, the T-wave alternans metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

For example, the heart rate variability in frequency metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

For example, the heart rate turbulence metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

For example, the QT interval variability metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

In some examples, the heartbeat variability metric is a combination of parameters. In some examples, the heartbeat variability metric may include a T-wave alternans metric, frequency metric, heart rate turbulence metric, or a QT interval variability metric. In one or more examples, a machine learning algorithm optimizes the weight of these parameters to determine when a threshold is exceeded to predict an upcoming arrhythmia.

In one or more examples, the heartbeat variability metric is a combination of parameters. In some examples, the heartbeat variability metric may include a T-wave alternans metric, frequency metric, heart rate turbulence metric, or a QT interval variability metric. In one or more examples, a machine learning algorithm optimizes the weight of these parameters to determine when a threshold is exceeded to predict an upcoming arrhythmia and where the parameters are corrected for one or more of the following activity level, medication, respiration level, heart rate, age, gender, weight, ST segment changes, time of the day (nocturnal, diurnal), comorbidities or disease progression, having diabetes 1 or 2. Medical device 720 or the external programmer (e.g. an implantable medical device (IMD)) may evaluate whether the heartbeat variability threshold is satisfied. If the heartbeat variability threshold of the metric is not satisfied, the IMD continues to sense the cardiac signal.

In some examples, if the heartbeat variability threshold of the metric is satisfied, the processing circuitry 758 may control electrical stimulation. For example, the therapy delivery circuity 752 may be controlled to deliver the electrical stimulation to the intercostal nerve based on the T-wave alternans metric satisfying the threshold. In some examples, the therapy delivery circuity 752 may be controlled to deliver the electrical stimulation to the intercostal nerve based on the heart rate variability in frequency metric satisfying the threshold. In some examples, the therapy delivery circuity 752 may be controlled to deliver the electrical stimulation to the intercostal nerve based on the heart rate turbulence metric satisfying the threshold. In some examples, the therapy delivery circuity 752 may be controlled to deliver the electrical stimulation to the intercostal nerve based on the QT interval variability metric satisfying the threshold.

If the heartbeat variability threshold of the metric is satisfied, the processing circuitry 758 may detect whether ventricular tachyarrhythmia (VT) or ventricular fibrillation (VF) is present, based on the cardiac signal. If VT or VF is detected, and medical device 720 is configured to deliver antitachyarrhythmia therapy, medical device 720 delivers defibrillation or other antitachyarrhythmia therapy to the patient.

If the processing circuitry does not detect VT or VF, processing circuitry 758 may control the therapy delivery circuitry 752 of a medical device to deliver electrical stimulation to an intercostal nerve of a patient via at least two of the plurality of electrodes 740, 734. In some examples, the electrical stimulation may be delivered with stimulation parameters configured to suppress ventricular tachyarrhythmia of the patient. In some examples, the stimulation parameters may be set such that stimulation may be delivered having a stimulation frequency less than or equal to 40 hertz (Hz) (808). In some examples, stimulation may be delivered having a stimulation frequency of 10 Hz. In some examples, stimulation may be delivered having a stimulation frequency of 20 Hz. In some examples, stimulation may be delivered having a stimulation frequency of 33 Hz. In some examples, stimulation may be delivered having a stimulation frequency of 40 Hz. In some examples, stimulation may be delivered having a stimulation frequency of 50 Hz. In one or more examples, stimulation parameters may include a 1 millisecond (ms) pulse width. In some examples, the pulse width may be shorter or longer than 1 ms.

If heartbeat variability threshold has been satisfied, neurostimulation may be delivered until the heartbeat variability threshold is no longer satisfied, or a certain time elapses. Memory 759 may store markers, stimulation parameters and outcomes and finetune the stimulation parameters. The processing circuitry 758 may direct neurostimulation to stop in the event arrhythmias are detected, and defibrillation therapy may be delivered if the medical device is configured to deliver therapy to treat the arrhythmia.

Memory 759 may be configured to store a variety of operational parameters, therapy parameters, sensed and detected data, and any other information related to the therapy and treatment of patient. In some examples, memory 758 may store sensed ECGs, e.g., associated with detected arrhythmias, and therapy parameters that define the delivery of therapy provided by therapy delivery circuitry 752. In other examples, memory 578 may act as a temporary buffer for storing data until it can be uploaded to an external device.

Communication circuitry 756 includes any suitable circuitry, firmware, software, or any combination thereof for communicating with another device, such as an external device. For example, communication circuitry 756 may include one or more antennae, modulation and demodulation circuitry, filters, amplifiers, or the like for radio frequency communication with other devices. Other examples of local wireless communication techniques that may be employed to facilitate communication, for example between external programmer and IMD include RF communication according to the 802.11 or Bluetooth® specification sets or other standard or proprietary telemetry protocols. In this manner, other external devices may be capable of communicating with external programmer without needing to establish a secure wireless connection. Processing circuitry 758 may provide the data to be uplinked to external device and the control signals for the telemetry circuit within communication circuitry 756, e.g., via an address/data bus. In some examples, communication circuitry 756 may provide received data to processing circuitry 58 via a multiplexer.

Power source 754 may be any type of device that is configured to hold a charge to operate the circuitry of ICD. Power source 754 may be provided as a rechargeable or non-rechargeable battery.

Figure 8:
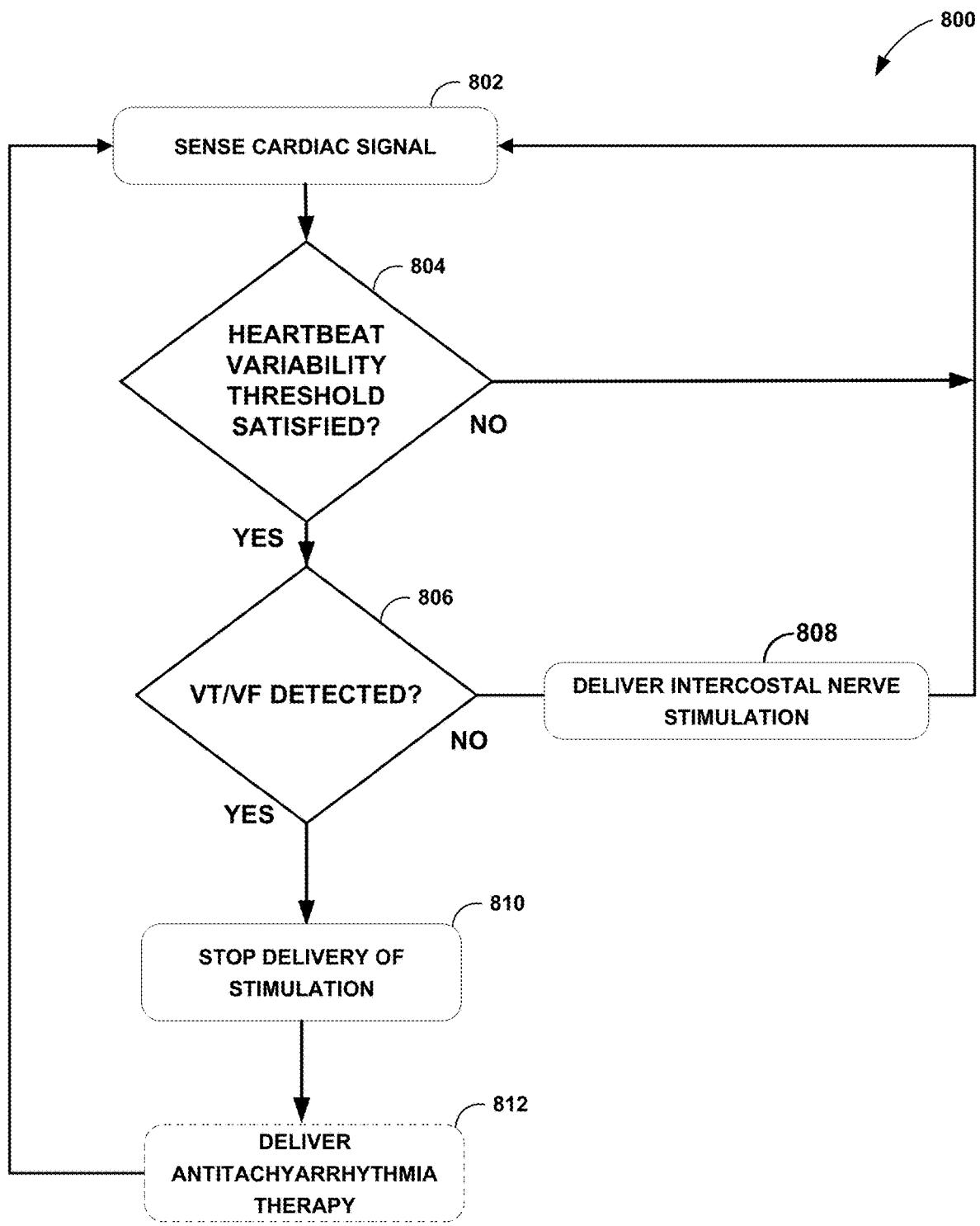
FIG. 8 is a flowchart illustrating an example operation of an implantable medical device according to the techniques of the disclosure.

FIG. 8 is a flowchart illustrating an example method of operation of a medical devices according to the techniques of the disclosure. For purpose of example, the example operation of FIG. 8 is described in reference to the example medical device system 100 of FIG. 1. However, the example operation of FIG. 8 is equally applicable to the example medical device system 500 of FIGS. 4-5. The medical device may be implanted within a patient, and may include a plurality of electrodes. In some examples, the method may include delivering electrical stimulation via the plurality of electrodes to an intercostal nerve of a patient via at least two of the plurality of electrodes. In one or more examples, the medical device may further include an implantable lead which may include at least one of the at least two of the plurality of electrodes. In some examples, the implantable lead may be configured to position the at least one electrode proximate to the intercostal nerve when implanted in the patient. In one or more examples, the plurality of electrodes may include a defibrillation electrode configured to deliver a defibrillation shock, where the defibrillation electrode may be carried by the implantable lead. In one or more examples, the medical device may include a housing that houses therapy delivery circuitry and processing circuitry, and the housing may be subcutaneously implanted within the patient. In some examples, the housing may be configured for subcutaneous implantation proximate to the intercostal nerve.

The example operation illustrated in FIG. 8 is shown for exemplary purposes only. The techniques as set forth in this disclosure may be implemented in the example operation (800) of FIG. 8, as well as other types of operations not described specifically herein.

Lead 110 is implanted in a patient, where lead 110 may include a plurality of electrodes 120A, 120B. At least one of medical device 140 or an external programmer may be used to sense cardiac signals of the patient (802), where the cardiac signal may include a cardiac electrogram sensed via at least two of the plurality of electrodes. In some embodiments, the medical device is implanted and the lead 110 may be disposed in a position to deliver electrical stimulation to an intercostal nerve of a patient via at least two of the plurality of electrodes 120A, 120B. The method may further include determining a heartbeat variability metric, for instance by the processing circuitry, where the heartbeat variability metric may be based on the cardiac signal. In some examples, the heartbeat variability metric may include a T-wave alternans metric. In some examples, the heartbeat variability metric may include a heart rate variability in frequency metric. In some examples, the heartbeat variability metric may include a heart rate turbulence metric. In some examples, the heartbeat variability metric may include a QT interval variability metric.

Once the heartbeat variability metric has been established, therapy delivery circuitry may deliver electrical stimulation to the intercostal nerve of a patient. Processing circuitry may control the therapy delivery circuitry to deliver the electrical stimulation. In some examples, therapy delivery circuitry may deliver the electrical stimulation based on the cardiac signal. The heartbeat variability metric may have one or more thresholds associated therewith.

For example, the T-wave alternans metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

For example, the heart rate variability in frequency metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

For example, the heart rate turbulence metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

For example, the QT interval variability metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

In some examples, the heartbeat variability metric is a combination of parameters. In some examples, the heartbeat variability metric may include a T-wave alternans metric, frequency metric, heart rate turbulence metric, or a QT interval variability metric. In one or more examples, a machine learning algorithm optimizes the weight of these parameters to determine when a threshold is exceeded to predict an upcoming arrhythmia.

In one or more examples, the heartbeat variability metric is a combination of parameters. In some examples, the heartbeat variability metric may include a T-wave alternans metric, frequency metric, heart rate turbulence metric, and/or a QT interval variability metric. In one or more examples, a machine learning algorithm optimizes the weight of these parameters to determine when a threshold is exceeded to predict an upcoming arrhythmia and where the parameters are corrected for one or more of the following activity level, medication, respiration level, heart rate, age, gender, weight, ST segment changes, time of the day (nocturnal, diurnal), comorbidities or disease progression, having diabetes 1 or 2.

The IMD or the external programmer may evaluate whether the heartbeat variability threshold is satisfied (804). If the heartbeat variability threshold of the metric is not satisfied, the IMD continues to sense the cardiac signal (802).

In some examples, if the heartbeat variability threshold of the metric is satisfied, the method may include the following. In some examples, the therapy delivery circuity may be controlled to deliver the electrical stimulation to the intercostal nerve based on the T-wave alternans metric satisfying the threshold. In some examples, the therapy delivery circuity may be controlled to deliver the electrical stimulation to the intercostal nerve based on the heart rate variability in frequency metric satisfying the threshold. In some examples, the therapy delivery circuity may be controlled to deliver the electrical stimulation to the intercostal nerve based on the heart rate turbulence metric satisfying the threshold. In some examples, the therapy delivery circuity may be controlled to deliver the electrical stimulation to the intercostal nerve based on the QT interval variability metric satisfying the threshold.

If the heartbeat variability threshold of the metric is satisfied, the processing circuitry may detect whether VT or VF is present, based on the cardiac signal (806). In some examples, if VT or VF is detected, delivery of stimulation is stopped (810). Optionally, defibrillation is applied to the patient (812), and then the cardiac signal is further sensed.

If the processing circuitry does not detect VT or VF, processing circuitry may control the therapy delivery circuitry of a medical device to deliver electrical stimulation to an intercostal nerve of a patient via at least two of the plurality of electrodes. In some examples, the electrical stimulation may be delivered with stimulation parameters configured to suppress ventricular tachyarrhythmia of the patient. In some examples, the stimulation parameters may be set such that stimulation may be delivered having a stimulation frequency less than or equal to 40 hertz (Hz) (808). In some examples, stimulation may be delivered having a stimulation frequency of 10 Hz. In some examples, stimulation may be delivered having a stimulation frequency of 20 Hz. In some examples, stimulation may be delivered having a stimulation frequency of 33 Hz. In some examples, stimulation may be delivered having a stimulation frequency of 40 Hz. In some examples, stimulation may be delivered having a stimulation frequency of 50 Hz. In one or more examples, stimulation parameters may include a 1 millisecond (ms) pulse width. Delivery of the electrical stimulation configured to suppress ventricular tachyarrhythmia may continue until the heartbeat variability metric is no longer satisfied, and/or may continue for a period of time.

For example, the T-wave alternans metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

In another example, the heart rate variability in frequency metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

In an example, the heart rate turbulence metric may have a threshold, where the threshold may be determined by population and/or medication of the patient. In some examples, the threshold for this metric would be satisfied if an average value as determined over 10 minutes is significantly more than 10% than the average values over a pre-determined window, for example within a time period of 24 hours.

In another example, the QT interval variability metric may have a threshold, where the threshold may be determined by population and/or medication of the patient. In some examples, the threshold for this metric would be satisfied if the average value as determined over 10 minutes is significantly more than 10% than the average values over a pre-determined window, for example within a time period of 24 hours.

In some examples, the medical device may monitor one or more heart variability metrics for upcoming arrhythmias or other deterioration of the heart status. When a heartbeat variability threshold has been satisfied, the medical device may deliver neurostimulation until the heartbeat variability of the cardiac signal moves back to normal range or a certain time elapses. The medical device may store markers, stimulation parameters and outcomes and finetune the stimulation parameters according to the results within certain boundaries by self-learning algorithms. The device may stop neurostimulation in the event an arrhythmia has been detected, and the ICD may deliver defibrillation therapy.

A computer-readable storage medium is further disclosed herein wherein the computer-readable storage medium may include instructions that, when executed by processing circuitry of a medical device comprising a plurality of electrodes, cause the medical device to: deliver electrical stimulation to an intercostal nerve of a patient via at least two of the plurality electrodes; wherein the electrical stimulation is delivered with stimulation parameters configured to suppress ventricular tachyarrhythmia of the patient, wherein the stimulation parameters comprise a stimulation frequency less than or equal to 40 hertz (Hz).

The following numbered examples may illustrate one or more aspects of this disclosure:

Example 1: A medical device includes a plurality of electrodes; therapy delivery circuitry; and processing circuitry configured to control the therapy delivery circuitry to deliver electrical stimulation to an intercostal nerve of a patient via at least two of the plurality of electrodes, wherein the electrical stimulation is delivered with stimulation parameters configured to suppress ventricular tachyarrhythmia of the patient, wherein the stimulation parameters comprise a stimulation frequency less than or equal to 40 hertz (Hz).

Example 2: The medical device of example 1, wherein the frequency is 10 Hz.

Example 3: The medical device of one of examples 1 or 2, wherein stimulation parameters comprise a 1 millisecond (ms) pulse width.

Example 4: The medical device of any one or more of examples 1-3, wherein the medical device is implantable.

Example 5: The medical device of any one or more of examples 1-4, further comprising an implantable lead comprising at least one of the at least two of the plurality of electrodes, the implantable lead configured to position the at least one electrode proximate to the intercostal nerve.

Example 6: The medical device of example 5, wherein the plurality of electrodes comprises a defibrillation electrode configured to deliver a defibrillation shock, the defibrillation electrode carried by implantable lead.

Example 7: The medical device of example 6, wherein at least one of the plurality of electrodes comprises a cardiac sensing electrode to sense a cardiac parameter.

Example 8: The medical device of any one or more of examples 1-7, further comprising a housing that houses the therapy delivery circuitry and the processing circuitry, wherein the housing is configured for subcutaneous implantation.

Example 9: The medical device of example 8, wherein at least one of the plurality of electrodes comprises a sensing electrode, and the housing is configured together with the cardiac sensing electrode to sense a cardiac signal.

Example 10: The medical device of any of examples 8 and 9, wherein the housing is configured for subcutaneous implantation proximate to the intercostal nerve.

Example 11: The medical device of example 10, wherein the housing comprises at least one of plurality electrodes via which the electrical stimulation is delivered.

Example 12: The medical device of any one or more of examples 1-11, further includes determine a heartbeat variability metric based on the cardiac signal; and control the therapy delivery circuitry to deliver the electrical stimulation to the intercostal nerve based on the heartbeat variability metric.

Example 13: The medical device of example 12, wherein the cardiac signal comprises a cardiac electrogram sensed via at least two of the plurality of electrodes.

Example 14: The medical device of example 13, wherein the cardiac signal is T-wave related changes, indices of dispersion of repolarization, QTV, QTc, ST interval, ST elevation, T wave amplitude, T peak to T end, T slope, T-wave area, T-wave asymmetry, R-wave/T-wave amplitude, and the variabilities thereof, T-wave alternans by beat to beat envelop analyses, autonomic markers, heart rate variability related markers in a time and frequency domain, heart rate turbulence onset and slope, or deceleration capacity.

Example 15: The medical device of example 14, wherein processing circuitry is configured to implement a machine learning algorithm that optimizes a weight of the cardiac signals to determine a representative threshold for an imminent ventricular arrhythmia.

Example 16: The medical device of example 15, wherein the machine learning algorithm corrects for one or more of medication, respiration level, heart rate, age, gender, weight, ST segment changes, time of the day (nocturnal, diurnal), comorbidities or disease progression, having diabetes 1 or 2.

Example 17: The medical device of any one or more of examples 12-16, wherein the heartbeat variability metric comprises a T-wave alternans metric, and processing circuitry is configured to: determine whether the T-wave alternans metric satisfies a threshold; and control the therapy delivery circuitry to deliver the electrical stimulation to the intercostal nerve when T-wave alternans metric satisfies the T-wave alternans threshold.

Example 18: The medical device of any one or more of examples 12-17, wherein the heartbeat variability metric comprises a heart rate variability in frequency metric, and processing circuitry is configured to: determine whether the heart rate variability in frequency metric satisfies a threshold; and control the therapy delivery circuitry to deliver the electrical stimulation to the intercostal nerve when heart rate variability in frequency metric satisfies the heart rate variability in frequency threshold.

Example 19: The medical device of any one or more of examples 12-18, wherein the heartbeat variability metric comprises a heart rate turbulence metric, and processing circuitry is configured to: determine whether the heart rate turbulence metric satisfies a threshold; and control the therapy delivery circuitry to deliver the electrical stimulation to the intercostal nerve when heart rate turbulence metric satisfies the heart rate turbulence threshold.

Example 20: The medical device of any one or more of examples 12-19, wherein the heartbeat variability metric comprises an QT interval variability metric, and processing circuitry is configured to: determine whether the QT interval variability metric satisfies a threshold; and control the therapy delivery circuitry to deliver the electrical stimulation to the intercostal nerve when QT interval variability metric satisfies the threshold.

Example 21: A method includes delivering electrical stimulation, by therapy delivery circuitry of a medical device further comprising processing circuitry and a plurality of electrodes, to an intercostal nerve of a patient via at least two of the plurality of electrodes; wherein delivering the electrical stimulation includes delivering with stimulation parameters configured to suppress ventricular tachyarrhythmia of the patient, wherein the stimulation parameters comprise a stimulation frequency less than or equal to 40 hertz (Hz).

Example 22: The method of example 21, wherein the frequency is 10 Hz.

Example 23: The method of one of examples 21 and 22, wherein stimulation parameters comprise a 1 millisecond (ms) pulse width.

Example 24: The method of any one or more of examples 21-23, wherein the medical device is implanted within the patient.

Example 25: The method of any one or more of examples 21-24, wherein the medical device further comprises an implantable lead comprising at least one of the at least two of the plurality of electrodes, the implantable lead positioning the at least one electrode proximate to the intercostal nerve.

Example 26: The method of example 25, wherein the plurality of electrodes comprises a defibrillation electrode configured to deliver a defibrillation shock, the defibrillation electrode carried by implantable lead.

Example 27: The method of any one or more of examples 21-26, wherein the medical device further comprises a housing that houses the therapy delivery circuitry and the processing circuitry, wherein the housing is subcutaneously implanted within the patient.

Example 28: The method of example 27, wherein the housing is subcutaneously implanted proximate to the intercostal nerve.

Example 29: The method of example 28, wherein the housing comprises at least one of the plurality of electrodes, and wherein delivering the electrical stimulation comprises delivering the electrical stimulation via the at least one electrode of the housing.

Example 30: The method of any one or more of examples 21-29, wherein the medical device further comprises sensing circuitry configured to sense a cardiac signal of the patient, the method further includes determining, by the processing circuitry, a heartbeat variability metric based on the cardiac signal; and controlling, by the processing circuitry, the therapy delivery circuitry to deliver the electrical stimulation to the intercostal nerve based on the heartbeat variability metric.

Example 31: The method of example 30, wherein the cardiac signal comprises a cardiac electrogram sensed via at least two of the plurality of electrodes.

Example 32: The method of any of examples 30 and 31, wherein the heartbeat variability metric comprises a T-wave alternans metric, and controlling the therapy delivery circuitry to deliver the electrical stimulation to the intercostal nerve comprises: determining whether the T-wave alternans metric satisfies a threshold; and controlling the therapy delivery circuitry to deliver the electrical stimulation based on the T-wave alternans metric satisfying the threshold.

Example 33: The medical device of any one or more of examples 30-32, wherein the heartbeat variability metric comprises a heart rate variability in frequency metric, and controlling the therapy delivery circuitry to deliver the electrical stimulation to the intercostal nerve comprises: determining whether the heart rate variability in frequency metric satisfies a threshold; and controlling the therapy delivery circuitry to deliver the electrical stimulation based on the heart rate variability in frequency metric satisfying the threshold.

Example 34: The medical device of any one or more of examples 30-33, wherein the heartbeat variability metric comprises a heart rate turbulence metric, and controlling the therapy delivery circuitry to deliver the electrical stimulation to the intercostal nerve comprises: determining whether the heart rate turbulence metric satisfies a threshold; and controlling the therapy delivery circuitry to deliver the electrical stimulation based on the heart rate turbulence metric satisfying the threshold.

Example 35: The medical device of any one or more of examples 30-34, wherein the heartbeat variability metric comprises a QT interval variability metric, and controlling the therapy delivery circuitry to deliver the electrical stimulation to the intercostal nerve comprises: determining whether the QT interval variability metric satisfies a threshold; and controlling the therapy delivery circuitry to deliver the electrical stimulation based on the QT interval variability metric satisfying the threshold.

Example 36: A computer-readable storage medium includes deliver electrical stimulation to an intercostal nerve of a patient via at least two of the plurality electrodes; wherein the electrical stimulation is delivered with stimulation parameters configured to suppress ventricular tachyarrhythmia of the patient, wherein the stimulation parameters comprise a stimulation frequency less than or equal to 40 hertz (Hz).

The techniques and devices disclosed herein are designed to prevent arrhythmias by intercostal subcutaneous nerve stimulation to reduce the frequency of ventricular tachyarrhythmia that need high voltage shocks in patients. As indicated by the experiments discussed below, electrical stimulation of the intercostal nerve has shown to affect autonomic balance in an acute series of healthy pigs and to prevent ventricular arrhythmia. In a previous acute pig study, a strong effect of nerve stimulation on a surrogate marker of sympathetic drive to the heart, which depended on frequency, was found. To extrapolate these effects on heart rate variability (HRV) to arrhythmia inducibility, experiments were performed in a pig post-myocardial infarct model and arrhythmia inducibility and refractory periods were assessed without and with stimulation at 10 and 40 Hz.

Eight pigs were subjected to microembolization of the left ventricle to induce a myocardial infarct (MI). Three weeks after the induction, the animals were anaesthetized and instrumented with 5 leads in the heart (1 atrial, 2 in the right and 2 in left ventricle), pressure catheters, ECG and one subcutaneous intercostal lead 8-polar between the second and third rib for nerve stimulation. The effect of nerve stimulation on arrhythmia inducibility was assessed and refractory periods in the right atrium and left and right ventricle and the effect on heart rate variability (HRV) in frequency spectrum to assess autonomic balance was investigated.

In the tables below numbers which may indicate a pro-arrhythmic effect are given in italic and anti-arrhythmic effect are given in underlined italic.

In Experiment 1 in a pig post-myocardial infarct model, a left ventricular lead in the base in the post-MI area dislodged and effective refractory periods (ERPs) were not assessed at this site. Next, a 20 minute stabilization period followed, during which was stimulated with 40 Hz at 5.5V and again ERPs were assessed 3 times shortly after each other. Refractory period was increased with 30 ms in the right atrial apendage suggesting an anti-arrhythmic effect in the right atrium. The ERP was decreased in the right ventricular apex with 40 ms (indicating a pro-arrhythmic effect in the right ventricle) but not in the right ventricular septum or left ventricular apex (see Table 1). Furthermore, spatial dispersion was decreased in the right ventricle from 40 ms to 10 ms, which is indicative of an anti-arrhythmic during 40 Hz stimulation. Heart rate variability could not be assessed reliably.

TABLE 1

Experiment 1; ERP measured without and with 40 Hz nerve stimulation

|  | ERP [ms] no stim | ERP [ms] 40 Hz stim |
|---|---|---|
| RA appendage | 240 | _270_ |
| RV1 (apex) | 300 | _260_ |
| RV2 (septal RVOT) | 260 | 270 |
| LV1 (apex) | 240 | 250 |

In Experiment 2, with the results shown in Table 2, the experiment was initiated with 10 Hz measurements instead of 40 Hz. Before the measurement of ERP at one condition, i.e. no nerve stimulation or nerve stimulation at 10 or 40 Hz (both at 0.8V) 20 minutes of stabilization periods at the same condition were given to prevent to some extent the carry-over effect. The ERP in the basal left ventricle next to the myocardial infarct site increased during 10 Hz at 0.8V with 50 ms from 240 to 290 ms and spatial dispersion decreased in the left ventricle from 60 ms to 10 ms due to 10 Hz stimulation (Table 2), which is both considered anti-arrhythmic. When the ERP the basal left ventricle was assessed during 40 Hz stimulation after a stabilization period of 20 minutes the ERP went back to baseline level of 230 ms again, if assuming that the 10 ms difference is due to measurement variance. In the RV1 apex and base and LV1 apex no effect of stimulation at 10 Hz and subsequently 40 Hz was shown. In a third experiment, the left ventricular lead in the base dislodged and ERPs were not assessed at this site. Before the measurement of ERP at one condition, i.e. no nerve stimulation or nerve stimulation at 10 or 40 Hz (both at 2.3V) 20 minutes of stabilization periods at the same condition were given to prevent to some extent the carry-over effect. Stimulation with 10 Hz at 2.3 V increased the ERP in the right ventricular septal wall with 40 ms from 240 to 280 ms, which is considered anti-arrhythmic. However, spatial dispersion was increased from 10 to 30 ms (Table 2) and could be considered pro-arrhythmic. Subsequently there was stimulated with 40 Hz at 2.3V and after a 20 minute stabilization period, ERPs and spatial dispersion was similar to baseline, if assuming that the 10 ms difference is due to measurement variance (Table 3). In the RV1 apex and LV1 apex (MI area) no effect of stimulation at 10 Hz and subsequently 40 Hz was shown.

The stabilization periods of experiment 2 and 3 were used to assess HRV-HF indicating parasympathetic drive and can be found in Table 2.

TABLE 2

Results of experiments 2 and 3

| Exp | RV apex Change in ERP at from baseline | RV base Change in ERP from baseline | RV Change in spatial dispersion from baseline | LV apex Change in ERP from baseline | LV base Change in ERP from baseline | LV Change in spatial dispersion from baseline | Change in RR interval ms [%] | Change in HF HRV [ms$^2$] (%) (0.17-0.4 Hz) from baseline |
|---|---|---|---|---|---|---|---|---|
| | | | | | | | | |
| Effect of 10 Hz stimulation compared with pre-baseline | | | | | | | | |
| 2 | 0 | 0 | 10 ms | −10 ms | 0 | 50 ms | −50 ms | −20 ms (3%) | +10.3 (285%) |
| 3 | 10 ms | 0 | 40 ms | +10 ms | +10 ms | — | — | +85 ms (13%) | 16.2 (351%) |
| Effect of 40 Hz stimulation compared with pre-baseline after 10 Hz stimulation. | | | | | | | | |
| 2 | 0 | 10 ms | 0 ms | 10 ms | 0 | −10 ms | +10 ms | +15 ms (2%) | 17.5 (486%) |
| 3 | 10 ms | −10 ms | −10 ms | 0 | +10 | — | — | 104 ms (16%) | 15.4 (334%) |

Stimulation with 40 Hz appeared to have a strong effect on HF HRV representing parasympathetic activity. In a previous series performed in an acute series in healthy pigs thus non-MI model, where the effect of 40 Hz stimulation was also determined immediately after baseline an average increase of 20% in HF HRV was found in 5 animals. The effect of 40 Hz on refractory periods is unclear since the 10 Hz stimulation shortly before might have biased the measurements. In the experiment where there is only stimulated with 40 Hz, an anti-arrhythmic effect in the atrium was shown. The effect on anti-arrhythmicity in the ventricle was unclear since a decrease of dispersion was shown, however an increase in local refractory period in the RV apex was found.

In review of the effect of 10 Hz stimulation on ventricles, it is noted in 2/2 experiments, there was a higher ERP in respectively left ventricle and right ventricle during 10 Hz than during no stimulation (see Table 2). The HF HRV was strongly increased during 10 Hz stimulation, rep 285 and 351%. These increases in HF-HRV were in the range of those found in previous series of an acute non-MI model (on average 288% increase, n=6), where we stimulated with 10 Hz intercostally. The increases in HF-HRV were in the range of those found in previous series of an acute non-MI model (on average 288% increase, n=6), where we stimulated with 10 Hz intercostally. The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical device comprising:
a plurality of electrodes configured to sense a cardiac signal of a patient;
therapy delivery circuitry; and
processing circuitry configured to:
determine a heartbeat variability metric based on the cardiac signal; and
control the therapy delivery circuitry to deliver electrical stimulation to an intercostal nerve of a patient via at least two electrodes of the plurality of electrodes in response to the heartbeat variability metric satisfying a threshold, wherein the electrical stimulation is delivered with stimulation parameters configured to suppress ventricular tachyarrhythmia of the patient, wherein the stimulation parameters comprise a stimulation frequency less than or equal to 40 hertz (Hz).

2. The medical device of claim 1, wherein the frequency is 10 Hz.

3. The medical device of claim 1, wherein stimulation parameters comprise a 1 millisecond (ms) pulse width.

4. The medical device of claim 1, further comprising an implantable lead comprising at least one electrode of the at least two electrodes of the plurality of electrodes, the implantable lead configured to position the at least one electrode proximate to the intercostal nerve.

5. The medical device of claim 4, wherein the plurality of electrodes comprises a defibrillation electrode configured to deliver a defibrillation shock, the defibrillation electrode carried by the implantable lead.

6. The medical device of claim 1, further comprising a housing that houses the therapy delivery circuitry and the processing circuitry, wherein the housing is configured for subcutaneous implantation.

7. The medical device of claim 6, further comprising sensing circuitry within the housing, wherein at least one electrode of the plurality of electrodes comprises a cardiac sensing electrode, and the sensing circuitry is configured to sense a cardiac signal via the sensing electrode and the housing.

8. The medical device of claim 6, wherein the housing is configured for subcutaneous implantation proximate to the intercostal nerve of the patient.

9. The medical device of claim 8, wherein the housing comprises at least one electrode of the at least two electrodes via which the electrical stimulation is delivered.

10. The medical device of claim 1, further comprising sensing circuitry configured to sense the cardiac signal of the patient, wherein the processing circuitry is configured to:
determine a second metric based on the cardiac signal; and
control the therapy delivery circuitry to deliver the electrical stimulation to the intercostal nerve based on the heartbeat variability metric and the second metric.

11. The medical device of claim 10, wherein the second metric comprises one or more of autonomic markers, heart rate turbulence onset and slope, or deceleration capacity.

12. The medical device of claim 10, wherein the second metric comprises a plurality of metrics, and the processing circuitry is configured to implement a machine learning algorithm that is applied to the heartbeat variability metric and at least one of the plurality of metrics to determine a risk of ventricular arrhythmia.

13. The medical device of claim 10, wherein the processing circuitry is configured to:
compare the second metric to a second threshold; and
control the therapy delivery circuitry to deliver the electrical stimulation to the intercostal nerve in response to the heartbeat variability metric satisfying the threshold and the second metric satisfying the second threshold.

14. The medical device of claim 1, wherein the cardiac signal comprises a cardiac electrogram sensed via at least two electrodes of the plurality of electrodes.

15. The medical device of claim 1, wherein the heartbeat variability metric comprises metric of variability of at least one of heart rate, repolarization, QT interval, ST interval, ST elevation, T wave amplitude, T peak to T end interval, T slope, T-wave area, T-wave asymmetry, R-wave/T-wave amplitude, or T-wave *alternans*.

16. A method comprising:
delivering electrical stimulation, by therapy delivery circuitry of a medical device further comprising processing circuitry and a plurality of electrodes, to an intercostal nerve of a patient via at least two electrodes of the plurality of electrodes in response to a heartbeat variability metric satisfying a threshold;
wherein delivering the electrical stimulation includes delivering with stimulation parameters configured to suppress ventricular tachyarrhythmia of the patient, wherein the stimulation parameters comprise a stimulation frequency less than or equal to 40 hertz (Hz).

17. The method of claim 16, wherein the stimulation frequency is 10 Hz.

18. The method of claim 16, wherein stimulation parameters comprise a 1 millisecond (ms) pulse width.

19. The method of claim 16, wherein the medical device is subcutaneously implanted within the patient proximate the intercostal nerve.

20. The method of claim 19, wherein delivering the electrical stimulation comprises delivering the electrical stimulation via the at least one electrode of a housing subcutaneously implanted within the patient proximate the intercostal nerve.

21. The method of claim 16, further comprising:
sensing, by sensing circuitry of the medical device, a cardiac signal;
determining, by the processing circuitry, a metric based on the cardiac signal; and
controlling, by the processing circuitry, the therapy delivery circuitry to deliver the electrical stimulation to the intercostal nerve based on the metric.

22. A computer-readable storage medium comprising instructions that, when executed by processing circuitry of a medical device comprising a plurality of electrodes, cause the medical device to:
deliver electrical stimulation to an intercostal nerve of a patient via at least two electrodes of the plurality electrodes in response to a heartbeat variability metric satisfying a threshold;
wherein the electrical stimulation is delivered with stimulation parameters configured to suppress ventricular tachyarrhythmia of the patient, wherein the stimulation parameters comprise a stimulation frequency less than or equal to 40 hertz (Hz).

\* \* \* \* \*